US009752165B2

(12) United States Patent
Brotherson

(10) Patent No.: US 9,752,165 B2
(45) Date of Patent: Sep. 5, 2017

(54) PROCESSES AND SYSTEMS FOR RECOVERING OIL FROM FERMENTATION PRODUCTS

(71) Applicant: Cellulosic Ethanol Technologies, LLC, Galva, IA (US)

(72) Inventor: Travis Brotherson, Holstein, IA (US)

(73) Assignee: Cellulosic Ethanol Technologies, LLC, Galva, IA (US)

( * ) Notice: Subject to any disclaimer, the term of this patent is extended or adjusted under 35 U.S.C. 154(b) by 445 days.

(21) Appl. No.: 14/176,988

(22) Filed: Feb. 10, 2014

(65) Prior Publication Data

US 2015/0225669 A1   Aug. 13, 2015

(51) Int. Cl.

| C12P 7/64 | (2006.01) |
|---|---|
| C11B 1/00 | (2006.01) |
| C11B 1/02 | (2006.01) |
| A23K 10/38 | (2016.01) |
| B01D 17/02 | (2006.01) |

(Continued)

(52) U.S. Cl.
CPC ............ *C12P 7/64* (2013.01); *A23K 10/38* (2016.05); *C11B 1/00* (2013.01); *C11B 1/02* (2013.01); *C11B 1/025* (2013.01); *B01D 17/0205* (2013.01); *C02F 1/24* (2013.01); *C12F 3/00* (2013.01); *Y02E 50/10* (2013.01); *Y02P 60/873* (2015.11)

(58) Field of Classification Search
CPC ... Y02E 50/343; Y02E 50/10; B01D 17/0205; B03D 1/00; C11B 1/00; C11B 1/025; C11B 1/02; C12P 7/64; A23K 10/38; C02F 1/24; C12F 3/00; Y02P 60/873

See application file for complete search history.

(56) References Cited

U.S. PATENT DOCUMENTS

| 1,967,938 | A | * | 7/1934 | Jantzen | ................. | B01D 1/18 |
|---|---|---|---|---|---|---|
| | | | | | | 55/400 |
| 2,493,166 | A | * | 1/1950 | Schmitz, Jr. | .......... | B01D 19/02 |
| | | | | | | 210/172.1 |

(Continued)

FOREIGN PATENT DOCUMENTS

| AU | WO 2008148729 A2 * | 12/2008 | ............ B01F 3/0446 |
|---|---|---|---|
| NL | EP 2196539 A1 * | 6/2010 | ................ C12P 5/02 |

(Continued)

OTHER PUBLICATIONS

Finkelstein et al.; *Applied Biochemistry and Biotechnology*; vols. 113-116 (*12 issues*); Spring 2004; "Biotechnology for Fuels and Chemicals The Twenty-Fifth Symposium"; pp. 1139-1159.

(Continued)

*Primary Examiner* — Amber R Orlando
*Assistant Examiner* — Stephen Hobson
(74) *Attorney, Agent, or Firm* — Myers Bigel, P.A.

(57) ABSTRACT

Processes and systems for recovering oil from a fermentation product are provided that optimize oil recovery during fermentation. The processes and systems described herein introduce a gas into the fermentation product in order to cause the oil within the fermentation product to separate therefrom, thereby facilitating its subsequent recovery. The processes and systems described herein can maximize the amount of oil that can be recovered during fermentation.

8 Claims, 2 Drawing Sheets

(51) Int. Cl.
*C12F 3/00* (2006.01)
*C02F 1/24* (2006.01)

(56) References Cited

U.S. PATENT DOCUMENTS

| | | | | |
|---|---|---|---|---|
| 3,415,654 | A * | 12/1968 | Zinn | C12C 11/003 426/16 |
| 3,693,325 | A * | 9/1972 | Muller | B01D 19/02 435/812 |
| 3,990,945 | A | 11/1976 | Huff et al. | |
| 4,069,149 | A * | 1/1978 | Jackson | C02F 1/24 210/195.1 |
| 4,503,079 | A * | 3/1985 | King | C12P 7/12 426/494 |
| 4,541,928 | A * | 9/1985 | Seymour | A01K 63/04 210/177 |
| 4,555,345 | A * | 11/1985 | Yoshida | B01D 17/00 210/705 |
| 4,717,669 | A * | 1/1988 | Feres | B01F 3/04531 261/89 |
| 5,024,937 | A * | 6/1991 | Penticoff | B01D 19/04 210/631 |
| 5,075,234 | A * | 12/1991 | Tunac | B01F 3/04602 261/122.1 |
| 5,951,875 | A * | 9/1999 | Kanel | B03D 1/02 210/703 |
| 6,660,506 | B2 | 12/2003 | Nguyen et al. | |
| 7,083,954 | B2 * | 8/2006 | Jakel | A23D 9/00 435/134 |
| 7,527,941 | B1 | 5/2009 | Hogen et al. | |
| 7,638,314 | B2 * | 12/2009 | Zappi | C02F 1/26 424/283.1 |
| 7,960,574 | B1 * | 6/2011 | Dickey | C11B 1/00 554/11 |
| 8,105,398 | B2 * | 1/2012 | Morgan | C11B 13/005 44/300 |
| 8,298,396 | B2 * | 10/2012 | Goetheer | C12P 7/40 205/687 |
| 8,603,789 | B2 | 12/2013 | Harlick | |
| 8,633,003 | B2 | 1/2014 | Brotherson | |
| 8,759,050 | B2 | 6/2014 | Brotherson | |
| 9,260,676 | B2 * | 2/2016 | Faulconbridge | B01D 11/0426 |
| 2003/0068813 | A1 * | 4/2003 | Rietschel | C12M 41/02 435/301.1 |
| 2004/0023349 | A1 | 2/2004 | Bisgaard-Frantzen et al. | |
| 2006/0004237 | A1 * | 1/2006 | Appel | A61L 11/00 585/241 |
| 2006/0051847 | A1 * | 3/2006 | Gunnarsson | A61K 8/361 435/134 |
| 2008/0260902 | A1 * | 10/2008 | Van Houten | A23D 9/00 426/18 |
| 2009/0008325 | A1 * | 1/2009 | Ju | B03D 1/008 210/606 |
| 2009/0017164 | A1 * | 1/2009 | Schisler | C12P 7/06 426/62 |
| 2009/0053777 | A1 | 2/2009 | Hennessey et al. | |
| 2010/0065128 | A1 | 3/2010 | Benson et al. | |
| 2010/0159552 | A1 | 6/2010 | Benson et al. | |
| 2010/0196979 | A1 | 8/2010 | Birkmire et al. | |
| 2010/0196994 | A1 * | 8/2010 | van Leeuwen | C12N 1/14 435/256.1 |
| 2010/0291630 | A1 * | 11/2010 | Cox | C12P 21/02 435/71.2 |
| 2011/0003355 | A1 * | 1/2011 | Clark | C07C 29/76 435/158 |
| 2011/0179841 | A1 | 7/2011 | Lu | |
| 2011/0293785 | A1 * | 12/2011 | Franklin | A23D 7/00 426/61 |
| 2012/0045545 | A1 | 2/2012 | Mielgo et al. | |
| 2012/0168387 | A1 * | 7/2012 | Tran | B03D 1/008 210/705 |
| 2012/0244591 | A1 * | 9/2012 | Brotherson | C12P 7/08 435/165 |
| 2013/0149757 | A1 * | 6/2013 | Day | C12P 7/16 435/160 |
| 2013/0149763 | A1 | 6/2013 | Brotherson | |
| 2013/0149764 | A1 | 6/2013 | Brotherson | |
| 2013/0164795 | A1 * | 6/2013 | Lowe | C12P 7/16 435/134 |
| 2013/0295623 | A1 * | 11/2013 | Gardner | C12N 1/12 435/134 |
| 2013/0338387 | A1 * | 12/2013 | Petrie | C11B 1/00 554/224 |
| 2014/0144815 | A1 * | 5/2014 | Liu | B03D 1/004 209/166 |
| 2014/0148588 | A1 * | 5/2014 | Schilling | C11B 1/10 536/18.2 |
| 2014/0212937 | A1 * | 7/2014 | Li | B01F 3/04496 435/139 |
| 2014/0371477 | A1 * | 12/2014 | Wood | C08L 91/00 554/8 |
| 2015/0011741 | A1 * | 1/2015 | Blank | C12P 19/44 536/18.2 |

FOREIGN PATENT DOCUMENTS

| | | | | | |
|---|---|---|---|---|---|
| NL | WO 2015130167 A1 * | 9/2015 | | ........ | B01D 19/0005 |
| WO | WO 2006/039354 A2 | 4/2006 | | | |
| WO | WO 2008/057993 A2 | 5/2008 | | | |
| WO | WO 2014043288 A1 * | 3/2014 | | ............... | C12P 7/16 |
| WO | WO 2015009485 A1 * | 1/2015 | | ............... | C11B 1/10 |

OTHER PUBLICATIONS

Saha et al., "Dilute Acid Pretreatment, Enzymatic Saccharification and Fermentation of Wheat Straw to Ethanol", Process Biochemistry, Dec. 31, 2005, vol. 40, pp. 3693-3700 See abstract; pp. 3694-3695.

Ladisch et al.; "Cellulose conversion in dry grind ethanol plants"; *Science Direct; Bioresource Technology* 99 (2008) 5157-5159; Copyright 2007 Published by Elsevier Ltd.

Mosier, N. et al., "Optimization of pH Controlled Liquid Hot Water Pretreatment of Corn Stover", Bioresource Technology, Mar. 10, 2005, vol. 96, pp. 1986-1993 See entire document.

"Production of Acetone-Butanol-Ethanol (ABE) using distillers dried grains with solubles (DDGS): Pentose sugar utilization and impact of degradation products"; *Midwest Consortium for Biobased Products & Bioenergy*; University of Illinois; Dr. Hans Blascheck, Dr. Thaddeus Ezeji; printed Feb. 14, 2011.

"Research Challenges and Opportunities for Cellulose Conversion Technology in a Dry Mill Pathway"; *Midwest Consortium for Biobased Products & Bioenergy*; Michael Ladisch, Nathan Mosier, Wally Tyner, Nancy Ho. Mira Sedlak; Lorre, Purdue University; Mike Cotta, Bruce Dien, Xin-Liang Li, Eduardo Ximenes, USDA NCAUR, Hans Blaschek, Thaddeus Ezeji, University of Illinois, Bruce Dale, Balan Venkatesh, Michigan State University, Brent Shanks, Iowa State University, John Verkade, Ames Laboratory, Gene Petersen, Golden Field Office DOE; printed Feb. 14, 2011.

* cited by examiner

PROCESSES AND SYSTEMS FOR RECOVERING OIL FROM FERMENTATION PRODUCTS

BACKGROUND

1. Field of the Invention

The present invention relates generally to fermentation processes and systems. More particularly, the present invention relates generally to oil recovery processes and systems for fermentation systems.

2. Description of the Related Art

The production of ethanol for use as a gasoline additive or a straight liquid fuel continues to increase as petroleum costs rise and environmental concerns become more pronounced. Ethanol is generally produced using conventional fermentation processes that convert the starch in plant-based feedstocks into ethanol. While ethanol is generally the desired product produced during fermentation, there are also a number of other byproducts produced during fermentation that also have commercial value such as, for example, the oil derived from the fermentation feedstocks.

In certain fermentation processes, it can be financially lucrative to separate the oil from the fermentation product in order to recover the valuable oil. Generally, the oil is removed from the fermentation product after the ethanol has been removed therefrom. This particular fermentation product is commonly referred to as "whole stillage." The oil is typically removed from whole stillage by processing the whole stillage in a decanter to separate it into a light phase and a heavy phase, removing the light phase from the decanter, and concentrating the light phase via evaporation until a desired solids concentration is achieved. This concentrated phase is commonly referred to as condensed distiller's solubles ("CDS"). The concentrated phase is then subjected to an oil separation step, which can involve heating, chemically treating, and centrifuging the concentrated phase. Generally, the minimum process involves centrifugation. These processes can generally recover 0.5 to 0.8 pounds of oil per bushel of grain. Unfortunately, the recovery processes described above are unable to recover a considerable portion of the oil in the fermentation product and, therefore, are unable to maximize the commercial value of the oil found in fermentation products.

Thus, there is a need for processes and systems that can maximize the recovery of the oil present in fermentation feedstocks.

SUMMARY

In one or more embodiments, the present invention concerns a method for recovering an oil from a fermentation product. The method comprises (a) fermenting an oil-containing biomass feedstock to thereby produce a fermentation product; (b) introducing a gas into the fermentation product to thereby form an oil-poor component and an oil-rich component comprising a free oil; and (c) separating the oil-rich component from the oil-poor component to thereby form a recovered oil-rich product comprising the free oil.

In one or more embodiments, the present invention concerns a method for recovering an oil from whole stillage. The method comprises (a) fermenting a whole stillage to thereby produce a fermentation product; (b) introducing a gas into the fermentation product to thereby form an oil-poor component and an oil-rich component comprising a free oil; and (c) separating the oil-rich component from the oil-poor component to thereby produce a recovered oil.

In one or more embodiments, the present invention concerns a method for recovering an oil from a fermentation product. The method comprises (a) fermenting an oil-containing biomass feedstock in a fermentation tank to thereby produce a fermentation product; (b) transferring the fermentation product to a secondary tank from the fermentation tank; (c) introducing a gas into the secondary tank to thereby separate the fermentation product into an oil-poor component and oil-rich component comprising a free oil; and (d) separating the oil-rich component from the oil-poor component to thereby produce a recovered oil.

In one or more embodiments, the present invention concerns a system for recovering an oil from a fermentation product. The system comprises (a) a fermentation tank configured to ferment an oil-containing biomass feedstock to thereby produce a fermentation product; (b) a gas injection system configured to introduce a gas into the fermentation tank that separates the fermentation product into an oil-poor component and oil-rich component comprising a free oil; and (c) an oil recovery apparatus configured to separate the oil-rich component from the oil-poor component.

BRIEF DESCRIPTION OF THE FIGURES

Embodiments of the present invention are described herein with reference to the following drawing figures, wherein.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

The present invention is generally directed to processes and systems for recovering oil from a fermentation product. More particularly, the present invention is generally directed to processes and systems that can maximize the recovery of oil from a fermentation product by introducing a gas into the fermentation product to separate the products therein. As described below in further detail, by introducing a gas into the fermentation product, the oil in the fermentation product can be more easily separated and recovered, thereby optimizing the oil recovery rates. As described below, the present invention allows the oil derived from oil-containing feedstocks to be separated at the fermentation stage, which can require less equipment and greatly increase oil recovery rates compared to prior art processes.

As discussed below, the oil recovery processes described herein can be optionally utilized in a primary fermentation process and/or a secondary fermentation process in order to maximize oil recovery.

Figure 1:
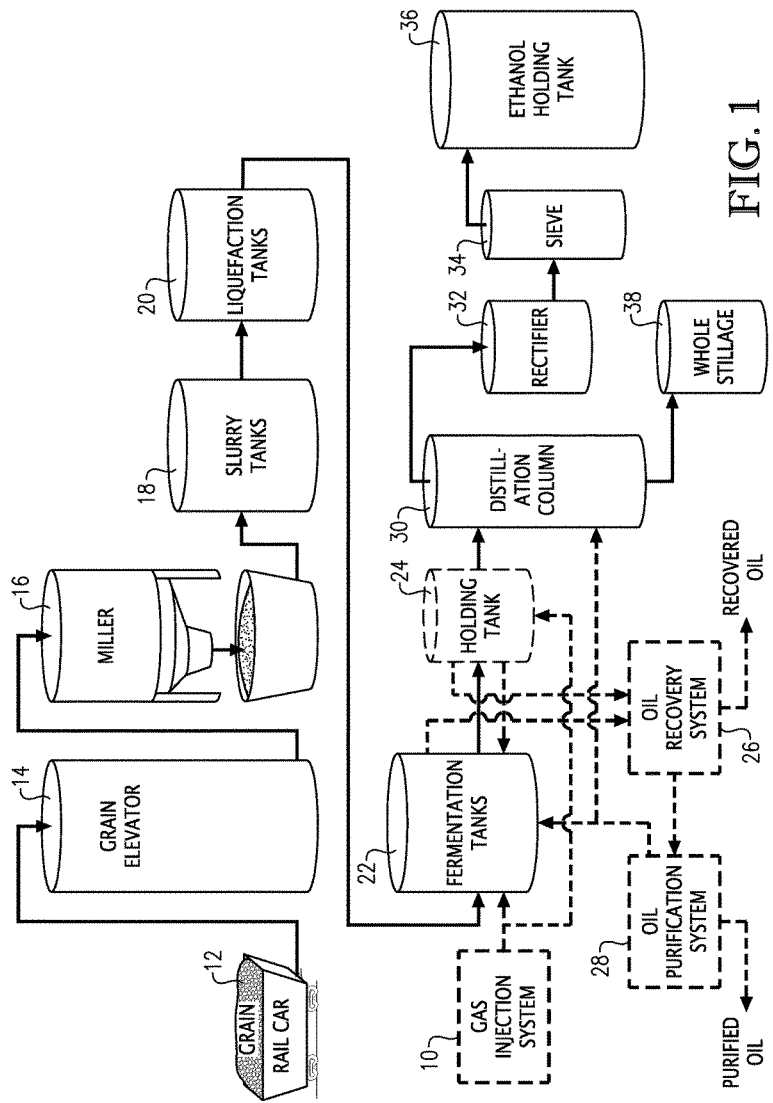
FIG. 1 is a flow diagram depicting an exemplary primary fermentation process utilizing an optional oil recovery step.

A primary fermentation process that can optionally utilize a gas injection system 10 is depicted in FIG. 1. However, it should be noted that the primary fermentation process depicted in FIG. 1 can be modified, in whole or part, by other fermentation steps or components without departing from the scope of the present invention. As used herein, "primary fermentation" refers to a fermentation process that utilizes a grain as a feedstock. Other fermentation processes are described and illustrated in U.S. Pat. Nos. 6,660,506, 7,527, 941, 8,288,138, and 8,409,640 and U.S. Patent Application Publication Nos. 2004/0023349, 2010/0021980, 2012/0045545, 2012/0244591, and 2013/0149764, all of which are incorporated herein by reference in their entireties.

Turning to FIG. 1, an oil-containing biomass 12 may be delivered to the ethanol production facility by any conventional means known in the art such as, for example, railcars, trucks, or barges. Generally, the oil-containing biomass comprises a grain such as, for example, barley, rye, wheat, oats, sorghum, milo, canola, corn, buckwheat, or a combination thereof. As shown in FIG. 1, a sufficient supply of the biomass to facilitate the primary fermentation process may be stored in one or more grain elevators 14.

Ethanol production can begin by milling or otherwise processing the biomass into a fine powder or flour by a hammer mill or other milling machine 16. The milled biomass can have an average particle size of at least about 100, 500, or 750 μm and/or not more than about 10, 5, or 2 mm. More particularly, the milled biomass can have an average particle size in the range of about 100 μm to 10 mm, 500 μm to 5 mm, or 750 μm to 2 mm. As used herein, "average particle size" refers to the average width of the milled biomass particles.

The milled biomass can then be mixed with water in one or more slurry tanks 18 to produce an initial biomass feedstock, which may also be referred to as a "mash." The initial biomass feedstock can comprise at least about 15, 25, 35, 40, or 50 and/or not more than about 90, 80, 75, 70, or 65 weight percent of solids. More particularly, the initial biomass feedstock can comprise in the range of about 15 to 90, 25 to 80, 35 to 75, 40 to 70, or 50 to 65 weight percent of solids. Additionally or alternatively, the initial biomass feedstock can comprise at least about 10, 15, 20, 25, 30, or 35 and/or not more than about 95, 90, 80, 75, 70, or 60 weight percent of starch. More particularly, the initial biomass feedstock can comprise in the range of about 10 to 95, 15 to 90, 20 to 80, 25 to 75, 30 to 70, or 35 to 60 weight percent of starch. It should be noted that all weight percentages described herein are based on total weight of the feedstock unless otherwise noted.

Furthermore, the initial biomass feedstock can comprise a significant amount of water from the slurry tanks 18. For example, the biomass feedstock can comprise at least about 10, 25, 40, or 50 and/or not more than about 85, 80, 75, or 65 weight percent of water. More particularly, the biomass feedstock can comprise in the range of about 10 to 85, 25 to 80, 40 to 75, or 50 to 65 weight percent of water.

The initial biomass feedstock for the primary fermentation can also include recycled components from previous fermentation processes, which can be added to the feedstock in the slurry tanks 18. For example, the initial biomass feedstock can comprise a whole stillage and/or thin stillage derived from a previous fermentation process. In one or more embodiments, the initial biomass feedstock can comprise at least about 0.5, 1, or 2 and/or not more than about 20, 10, or 5 weight percent of a thin stillage recycled from a previous fermentation process. More particularly, the initial biomass feedstock can comprise in the range of about 0.5 to 20, 1 to 10, or 2 to 5 weight percent of a thin stillage derived from a previous fermentation process. Furthermore, in such embodiments, at least 5, 20, or 40 and/or not more than about 95, 80, or 60 percent of the water in the biomass feedstock can be derived from the thin stillage.

As shown in FIG. 1, the initial biomass feedstock can then be mixed with enzymes in a liquefaction tank 20 and held in this tank for a sufficient amount of time to enable the enzymes to begin hydrolyzing the starch in the feedstock into fermentable sugars. In certain embodiments, the amount of enzyme activity in this step, especially if gluco-amylase is utilized, may be maintained at lower levels in order to leave more long chain sugars in the biomass feedstock. The enzymes can comprise, for example, a protease, alpha-amylase, gluco-amylase, xylanase, cellobiohydrolase, beta-glucosidase cellulase, amylase, hemicellulase, or combinations thereof. The enzymes may be added at a concentration in the range of about 0.001 to 0.5, 0.005 to 0.3, or 0.01 to 0.2 weight percent based on the dry weight of the solids. The temperatures and conditions for this treatment can vary depending on the type of enzymes used. During this treatment, at least 10, 20, or 30 and/or not more than 90, 70, or 60 percent of the starch present in the biomass feedstock can be hydrolyzed into long chain sugars. More particularly, this treatment can hydrolyze in the range of 10 to 90, 20 to 70, or 30 to 60 percent of the starch into long chain sugars.

Turning again to FIG. 1, the treated biomass feedstock is introduced into one or more fermentation tanks 22 wherein one or more yeast types are added to facilitate fermentation. In various embodiments, the added yeast comprises *Saccharomyces cerevisiae*. The primary fermentation process produces a primary fermentation product that can comprise alcohols, oil, and various other solid and liquid byproducts. The primary fermentation product may also be commonly referred to as "beer" by those skilled in the art. The primary fermentation step described herein can convert at least about 50, 75, 85, or 95 percent of the starch originally found in the biomass into the primary fermentation product.

The primary fermentation can occur over a time period in the range of 12 to 150, 24 to 130, or 36 to 110 hours. Furthermore, depending on the type of yeasts used, the primary fermentation can generally occur at a temperature in the range of 50 to 140, 70 to 120, or 80 to 97° F. In addition, the primary fermentation can occur at a pH in the range of about 3 to 8, 3.5 to 6, or 4 to 5.

In order to compensate for the possible high viscosity of the feedstock due to its solids content, a larger amount of alpha-amylase enzymes can be added to the feedstock before fermentation during the liquefaction step or during fermentation itself. Consequently, these enzymes can break down some of the starch in the feedstock, thereby reducing the viscosity of the biomass feedstock. Thus, the feedstock can be easier to move throughout the system depicted in FIG. 1. In various embodiments, the alpha-amylase can be derived solely from the grain used as the biomass feedstock, which have been genetically modified to express higher quantities of this enzyme. In such embodiments, additional alpha-amylase can be added or withheld. In embodiments where alpha-amylase is added, it may be added at a concentration in the range of about 0.001 to 0.5, 0.005 to 0.3, or 0.01 to 0.2 weight percent based on the dry weight of the solids.

As noted above, the primary fermentation product can comprise multiple types of alcohols, oil, and other various solid and liquid byproducts. However, ethanol is usually the most important product produced during the primary fermentation process. In one or more embodiments, the primary fermentation product can comprise at least about 7, 10, 13, or 15 and/or not more than about 40, 35, 30, or 25 weight percent of ethanol. More particularly, the primary fermentation product can comprise in the range of about 7 to 40, 10 to 35, 13 to 30, or 15 to 25 weight percent of ethanol. Furthermore, the primary fermentation can produce at least about 1.3, 2.1, 2.25, 2.4, or 2.65 and/or not more than about 3.8, 3.5, 3.3, 3.1, or 2.9 gallons of ethanol per bushel of grain. More particularly, the primary fermentation can produce in the range of about 1.3 to 3.8, 2.1 to 3.5, 2.25 to 3.3, 2.4 to 3.1, or 2.65 to 2.9 gallons of ethanol per bushel of grain.

Other byproducts included in the primary fermentation product can include, for example, glycerol, acetic acid, lactic acid, and carbon dioxide. In one or more embodiments, the primary fermentation product can comprise at least about 0.1, 0.5, or 1 and/or not more than about 5, 3, or 2 weight percent of glycerol. More particularly, the primary fermentation product can comprise in the range of about 0.1 to 5, 0.5 to 3, or 1 to 2 weight percent of glycerol. Furthermore, the primary fermentation product can comprise at least about 0.001, 0.005, or 0.01 and/or not more than about 0.5, 0.3, or 0.2 weight percent of acetic acid. More particularly, the primary fermentation product can comprise in the range of about 0.001 to 0.5, 0.005 to 0.3, or 0.01 to 0.2 weight percent of acetic acid. In addition, the primary fermentation product can comprise at least about 0.001, 0.005, or 0.01 and/or not more than about 2, 1.5, or 1 weight percent of lactic acid. More particularly, the primary fermentation product can comprise in the range of about 0.001 to 2, 0.005 to 1.5, or 0.01 to 1 weight percent of lactic acid. It should be noted that the above weight percentages are based on the total weight of the fermentation product unless otherwise noted.

Furthermore, the primary fermentation product can comprise one or more oils derived from the grain used as the fermentation feedstock. Like the other byproducts in the primary fermentation product, the oils in the primary fermentation product can also have commercial value. In one or more embodiments, the primary fermentation product can comprise at least about 0.1, 0.5, 1, or 2 and/or not more than 30, 25, 20, or 10 weight percent of oil derived from the oil-containing biomass feedstock. More particularly, the primary fermentation product can comprise in the range of about 0.1 to 30, 0.5 to 25, 1 to 20, or 2 to 10 weight percent of oil derived from the oil-containing biomass feedstock.

Moreover, in various embodiments, at least a portion of the oil in the primary fermentation product can be "free oil." As used herein, "free oil" is oil that is not bound in an emulsion within the fermentation product or trapped within a solid portion of the residual oil-containing biomass in the fermentation product. In one or more embodiments, the primary fermentation product can comprise at least about 0.1, 0.5, 1, or 2 and/or not more than 30, 25, 20, or 10 weight percent of free oil. More particularly, the primary fermentation product can comprise in the range of about 0.1 to 30, 0.5 to 25, 1 to 20, or 2 to 10 weight percent of free oil.

As previously noted, the oil in the primary fermentation product has commercial value and, thus, it can be desirable to remove this byproduct at some point from the fermentation product. Unlike the prior art processes, the processes and systems described herein are able to separate and extract the oil in the fermentation product prior to removing the ethanol from the fermentation product.

In various embodiments, the free oil in the primary fermentation product can be brought to the surface of the fermentation product by introducing a gas into the fermentation product. In such embodiments, the introduced gas can cause the oil in the fermentation product to rise to the top of the fermentation product, thereby making it easier to recover. The free oil that agglomerates at the top of the fermentation product can form a layer of free oil that is easily recoverable. In these embodiments, the introduced gas can form microscopic bubbles that can combine to form larger bubbles of gas. As these bubbles rise, they can form a convective flow of gas through the fermentation product that can bring droplets of free oil to the surface of the fermentation product. During this time, the free oil can become attached or encapsulated within these bubbles, thus allowing the free oil to rise to the top of the fermentation product. Thus, introducing a gas into the fermentation product can allow microscopic globules of oil to rise and coalesce, thereby creating a recoverable free oil layer.

Thus, in various embodiments, a gas may be introduced into the primary fermentation product in order to separate the fermentation product into an oil-poor component and an oil-rich component comprising the free oil. As used herein, "oil-poor" and "oil-rich" refer to the oil content of the separated components relative to the oil content of the original component from which the separated components are derived. Thus, an oil-rich component contains a greater weight percentage of oil than the component from which it is derived, while an oil-poor component contains a lesser weight percentage of oil than the component from which it is derived. In the present case, the oil-rich component contains a higher weight percentage of oil compared to the primary fermentation product, while oil-poor component contains a lower weight percentage of oil compared to the primary fermentation product.

In one or more embodiments, the gas introduced into the primary fermentation product can be at least partially derived from, or alternatively, entirely derived from, the gas produced during the primary fermentation by the yeasts and/or a gas introduced from the gas injection system 10. The gas can comprise one or many types of gases. In various embodiments, the gas comprises carbon dioxide, air, nitrogen, or combinations thereof. In certain embodiments, the gas comprises carbon dioxide.

In various embodiments, the gas can be introduced into the primary fermentation product through the use of an optional gas injection system 10, which can pump a gas stream into the bottom of the fermentation tank 22. In one or more embodiments, the gas injection system 10 can be configured to pump the gas into the fermentation tank at a sufficient pressure that can overcome the head pressure of the fermentation tank. The gas injection system can comprise any system known in the art that is capable of injecting a gas into the fermentation tank. For example, the gas injection system can comprise a gas sparger, gas diffuser, aeration turbine, venturi tube, fan, air pump, or a combination thereof.

In various embodiments, the gas introduced into the primary fermentation product can be at least partially derived, or alternatively, entirely derived from the gases produced during fermentation by the yeasts. As the yeasts ferment the sugars in the feedstock, various gases can be produced, such as carbon dioxide.

In certain embodiments, it may be difficult or impose a safety risk to remove oil from the top of an active fermenter. In these cases, it may be reasonable to process the fermentation product through any number of additional steps until it is safe to remove the oil from the top of tank. These additional process steps are discussed below and can include, for example, distillation, pressing, and centrifugation. The tankable liquids left after these processes can then be subjected to gas bubbling by means of the gas injection system 10 in an optional holding tank 24 as shown in FIG. 1.

The optional holding tank 24 as shown in FIG. 1 can be used to hold the fermentation product after it has been subjected to any number of post-fermentation treatment steps, but prior to being separated into oil-poor and oil-rich components as described above. In various embodiments, the primary fermentation product can be introduced into an optional holding tank 24. While in the holding tank 24, a gas can be introduced into the fermentation product, thereby separating the fermentation product into the oil-poor and oil-rich components discussed above. In such embodiments, the gas can be introduced into the holding tank 24 from the gas injection system 10. It should be noted that the gas introduced into the holding tank 24 will generally come from the gas injection system 10 since most of the fermentation will be finished by this point. An advantage of the gas injection system is that the primary fermentation product can be separated in non-fermentation tanks.

During the gas introduction steps, the gas can be introduced into the fermentation product while in the fermentation tanks and/or holding tank at a sufficient rate so as to cause the fermentation product to separate into the oil-poor and oil-rich components. In various embodiments, the gas can be introduced into the fermentation product at a rate of at least about 1, 5, 10, 15, 20, 25, 30, 35, 40, or 45 $cm^3$/min and/or not more than about 1,000, 750, 500, 400, 350, 300, 250, 200, 150, or 100 $cm^3$/min. More particularly, the gas can be introduced into the fermentation product at a rate in the range of about 1 to 1,000, 5 to 750, 10 to 500, 15 to 400, 20 to 350, 25 to 300, 30 to 250, 35 to 200, 40 to 150, or 45 to 100 $cm^3$/min. Furthermore, the gas can be introduced into the fermentation product over a time period of at least 0.1, 0.5, 1, 2, or 3 hours and/or not more than 24, 12, 10, 8 or 6 hours. More particularly, the gas can be introduced into the fermentation product over a time period in the range of 0.1 to 24 hours, 0.5 to 12 hours, 1 to 10 hours, 2 to 8 hours, or 3 to 6 hours.

An analysis of oil recovery through gravity separation in a stagnant fermentation medium with a viscosity of 100 centipoise showed that a spherical oil droplet of 1 mm in diameter will take several days to rise one meter without the aid of gas bubbling. These observations indicated that gas bubbling can be necessary to produce a recoverable layer of free-oil in a reasonable time frame.

Furthermore, it has been observed that agitation rates within the fermentation tanks 22 and/or holding tank 24 can affect the separation of the primary fermentation product into the oil-poor and oil-rich components during the gas introduction steps. By holding agitation rates to a low level, at least a portion of the free oil was able to float to the top of the fermentation product. In such cases, as long as the agitation rates were not high enough to cause a downward velocity that overcomes the buoyancy of the oil, the free oil can continue to float and be recovered. If the fermentation product is subjected to excessive agitation, then the free oil can be redistributed within the fermentation product as bound oil. As used herein, "bound oil" is oil in an emulsion or trapped within the solid portions of the residual biomass feedstock.

In many embodiments, the fermentation tanks 22 can have an agitator for agitating the fermentation product during fermentation. These agitators can include, for example, a mechanical agitator, mechanical stirrer, liquid recirculator, liquid pump, liquid injector, or gas pump. As one skilled in the art would appreciate, the agitation rate will vary depending on the size of the tank used for fermentation. For example, a laboratory scale bioreactor can utilize an agitator speed in the range of 300 to 900 revolutions per minute ("RPM") during fermentation, whereas a commercial tank capable of holding 100,000 to 1,000,000 liters can utilize an agitator speed in the range of 1 to 50 RPM. Thus, in various embodiments, the agitation rate of the agitator in the fermentation tank can be closely regulated during the gas introduction step so as to not interfere with the separation of the fermentation product into the oil-poor and oil-rich components. For example, the agitation rate of the agitator during the gas introduction step can be less than 100, 50, 20, 5, or 1 RPM. Furthermore, in embodiments where the gas introduction step occurs in the fermentation tank, the agitation speed of the agitator during the gas introduction can be at least 50, 75, 90, or 99 percent less than the agitation speed of the agitator during fermentation prior to the gas being introduced.

In various embodiments, the fermentation product is subjected to substantially no agitation or no agitation during the gas introduction step. As used herein, "substantially no agitation" refers to embodiments where agitation is not purposely applied such as, for example, through the use of an agitator, but does include incidental agitation that may be the consequence of the environment surrounding the tank.

It should be noted that the gas introduction step can occur during fermentation or after fermentation when the yeasts have finished converting the sugars into the various fermentation products. As noted above, the gas introduction step, and the subsequent removal of the oil-rich component, can occur in the fermentation tanks 22 or holding tank 24.

Turning back to FIG. 1, after separating the primary fermentation into the oil-poor and oil-rich components in the fermentation tanks 22 and/or optional holding tank 24, the oil-rich component can be recovered from the fermentation tanks 22 and/or the holding tank 24 using an oil recovery system 26. The oil recovery system can comprise any system or means known in the art that are capable of removing the top oil-rich component from the tanks such as, for example, a pumping apparatus or industrial pipette. For example, the oil recovery system could comprise a pipe and pump connected to the tank that could remove the top layer comprising the oil-rich component. In such embodiments, the pipe and pump could also remove the top 1% of the fermentation product to ensure that most, if not all, of the free oil is recovered from the fermentation tank.

The recovered oil-rich component removed by the oil recovery system 26 can contain the majority of the free oil originally found in the fermentation product. For example, the recovered oil-rich component can comprise at least about 25, 50, 75, 90, 95, or 99 percent of the free oil originally present in the fermentation product. Furthermore, the recovered oil-rich component can comprise at least about 25, 50, 75, 85, 90, 95, or 99 weight percent of oil. Moreover, the recovered oil-rich component may comprise an oil content by weight percentage that is at least 25, 50, 75, or 90 percent greater than the oil content by weight percentage of the primary fermentation product.

In addition to its high oil content, the recovered oil-rich component may also comprise some incidental fermentation byproducts. These incidental fermentation byproducts can include any of the other products produced during fermentation such as, for example, ethanol, glycerol, acetic acid, lactic acid, and unconverted biomass feedstock. Generally, the recovered oil-rich component can comprise less than about 20, 10, 5, 1, or 0.1 weight percent of incidental fermentation byproducts. Moreover, the recovered oil-rich component can comprise less than about 20, 10, 5, 1, or 0.1 weight percent of water.

In various embodiments, it may be desirable to further treat the recovered oil-rich component in an oil purification system 28 as shown in FIG. 1 in order to concentrate the oil and remove the undesirable byproducts therein. The oil purification system can comprise any system known in the art that is capable of purifying oil such as, for example, a filter membrane, a centrifuge, a settling tank, or a combination thereof. In one or more embodiments, the oil-rich component can be transferred to a settling tank in order to separate the residual fermentation product from the free oil. While in the settling tank, the heavier residual fermentation product should sink to the bottom. The heavier residual fermentation product can then be recycled back to the fermentation tank 22 for further conversion or sent to the distillation column 30 for further processing. Additionally or alternatively, the recovered oil-rich component can be processed in a centrifuge in order to separate the residual fermentation product and the free oil. Furthermore, the oil purification system can utilize one or more surfactants to facilitate the separation of the incidental fermentation products and the free oil.

The purified oil from the oil purification system 28 can comprise at least about 50, 85, 95, 99, or 99.9 weight percent of oil that was derived from the oil-containing biomass feedstock used in the fermentation process. Furthermore, the purified oil can comprise less than about 5, 3, 1, 0.1, or 0.01 weight percent of water. Moreover, the purified oil can comprise less than about 10, 5, 3, 1, or 0.1 weight percent of incidental fermentation byproducts.

In various embodiments, the primary fermentation can produce at least about 0.25, 0.5, 0.75, or 1 and/or not more than about 4, 3, 2.5, or 2 pounds of recovered oil per bushel of grain. More particularly, the primary fermentation can produce in the range of about 0.25 to 4, 0.5 to 3, 0.75 to 2.5, or 1 to 2 pounds of recovered oil per bushel of grain. Similarly, the primary fermentation can produce at least about 0.1, 0.2, 0.3, or 0.4 and/or not more than about 5, 4, 3, or 1 liters of recovered oil per bushel of grain. More particularly, the primary fermentation can produce in the range of about 0.1 to 5, 0.2 to 4, 0.3 to 3, or 0.4 to 1 liters of recovered oil per bushel of grain.

As noted above, the incidental fermentation product removed by the oil purification system 28 can be recycled back to the fermentation tank 22 for further conversion and/or sent to the distillation column 30 for further processing.

As shown in FIG. 1, after recovering the oil-rich component, the oil-poor component remains in the fermentation tank 22 and/or holding tank 24. The remaining oil-poor component generally comprises the non-oil byproducts produced during fermentation. For example, the oil-poor component generally comprises ethanol, glycerol, acetic acid, lactic acid, unconverted biomass feedstock, and other fermentation-derived alcohols. In one or more embodiments, the oil-poor component can comprise at least about 10, 15, 20, or 25 and/or not more than about 70, 60, 50, or 40 weight percent of ethanol. More particularly, the oil-poor component can comprise in the range of about 10 to 70, 15 to 60, 20 to 50, or 25 to 40 weight percent of ethanol. Furthermore, the oil-poor component comprises less than 20, 10, 5, or 1 weight percent of oil. Additionally or alternatively, the oil-poor component can comprise an oil content by weight percentage that is at least 25, 50, 75, or 90 percent lower than the oil content by weight percentage of the primary fermentation product. In embodiments where a holding tank 24 is utilized, the remaining oil-poor component in the holding tank 24 can be sent to the fermentation tanks 22 for further fermentation if necessary.

Turning again to FIG. 1, the remaining oil-poor component or primary fermentation product (for embodiments where the oil has not been removed during fermentation) in the fermentation tanks 22 or holding tank 24 can be transferred to one or more distillation columns 30, which are also known in the art as "beer strippers," in order to separate the alcohols, especially ethanol, from the solids and other liquids. The alcohol exits the top of these columns 30 and can be transferred to one or more rectifiers 32 to further remove moisture from the alcohol. The alcohol may also be passed to one or more molecular sieves 34 in order to remove even more moisture. The final alcohol can then be transferred to one or more ethanol holding tanks 36 where it may be denatured before use as a fuel or fuel additive.

The liquid and solid mixture that remains in the distillation columns 30 after the alcohol has been removed is commonly referred to as "whole stillage" or simply "stillage." The mixture can also be commonly referred to as "distiller's grains" or "spent distiller's grains." The whole stillage generally settles to the bottom of the distillation columns 30 and can then be transferred to one or more whole stillage holding tanks 38.

The whole stillage can comprise at least about 10, 12, 20, or 25 and/or not more than about 60, 55, 50, or 45 weight percent of solids. More particularly, the whole stillage can comprise in the range of about 10 to 60, 12 to 55, 20 to 50, or 25 to 45 weight percent solids. Additionally or alternatively, the whole stillage can comprise at least about 5, 15, 25, or 40 and/or not more than about 90, 70, 60, or 50 weight percent of water. More particularly, the whole stillage can comprise in the range of about 5 to 90, 15 to 70, 25 to 60, or 40 to 50 weight percent of water.

Although not shown in FIG. 1, the whole stillage produced by the primary fermentation step can have a number of uses. For example, the whole stillage may be optionally passed through one or more centrifuges, which can separate it into a stream of thin stillage and a stream of wet distiller's grain. Some or all of the thin stillage may be transferred to one or more evaporators to produce an evaporated thin stillage, which is commonly referred to as "syrup." The syrup may be used as an animal feed additive. Furthermore, the wet distiller's grain may be dried to produce a dried distiller's grain, which may also be utilized as a livestock feed.

Unlike conventional fermentation processes, the processes and systems described herein do not discard the whole stillage, but can use this byproduct to produce additional ethanol and oil. In various embodiments, the whole stillage produced during the primary fermentation can be subjected to a secondary fermentation step in order to maximize oil and ethanol production. One advantage of employing the secondary fermentation described herein is that it can be utilized to maximize oil and ethanol production from the byproducts derived from the primary fermentation step rather than just using the byproducts as animal feed.

Moreover, in certain embodiments, the secondary fermentation can be used to release the oil trapped in the various fiber components of the whole stillage. It has been observed that processing of the cellulosic portion during the secondary fermentation can allow the oil trapped within the fibers of the whole stillage to be released in much greater quantities compared to conventional processes. During this process, the fiber in both the pericarp and the germ, which are oil rich portions of the grain, can be broken down. As described below, this can be accomplished through a combination of thermal, chemical, mechanical, and enzymatic means. As the fiber is broken down, the bound oil can be released from the fiber matrix. At the same time, simple sugars are being produced and fermented.

Since whole stillage is generally the byproduct of the fermentation of corn or other cereal grain, it can contain a sizable fraction of fiber. All fiber is made up of hemicellulose, cellulose, and lignin. Cellulose consists of glucose molecules, the same as in starch, but the linkages in cellulose make it more difficult to break down into individual glucose molecules than in starch. Hemicellulose contains a mixture of sugars and is generally easier to breakdown than cellulose. Lignin and/or pectin functions as a binder and cannot generally be broken down into fermentable sugars. The processes of the present invention can also include steps for converting both the hemicellulose and cellulose portions of the whole stillage into sugars that may be fermented into ethanol.

Prior to the secondary fermentation, the whole stillage can be subjected to (1) prolonged soaking in the liquefaction tanks, (2) heating in the distillation columns, and/or (3) chemical reactions from the various chemical additives added during the primary fermentation. Consequently, these previous steps can help facilitate the breakdown of the fibers in the whole stillage and make them more inclined to release the oil within the fibers during the secondary fermentation.

Figure 2:
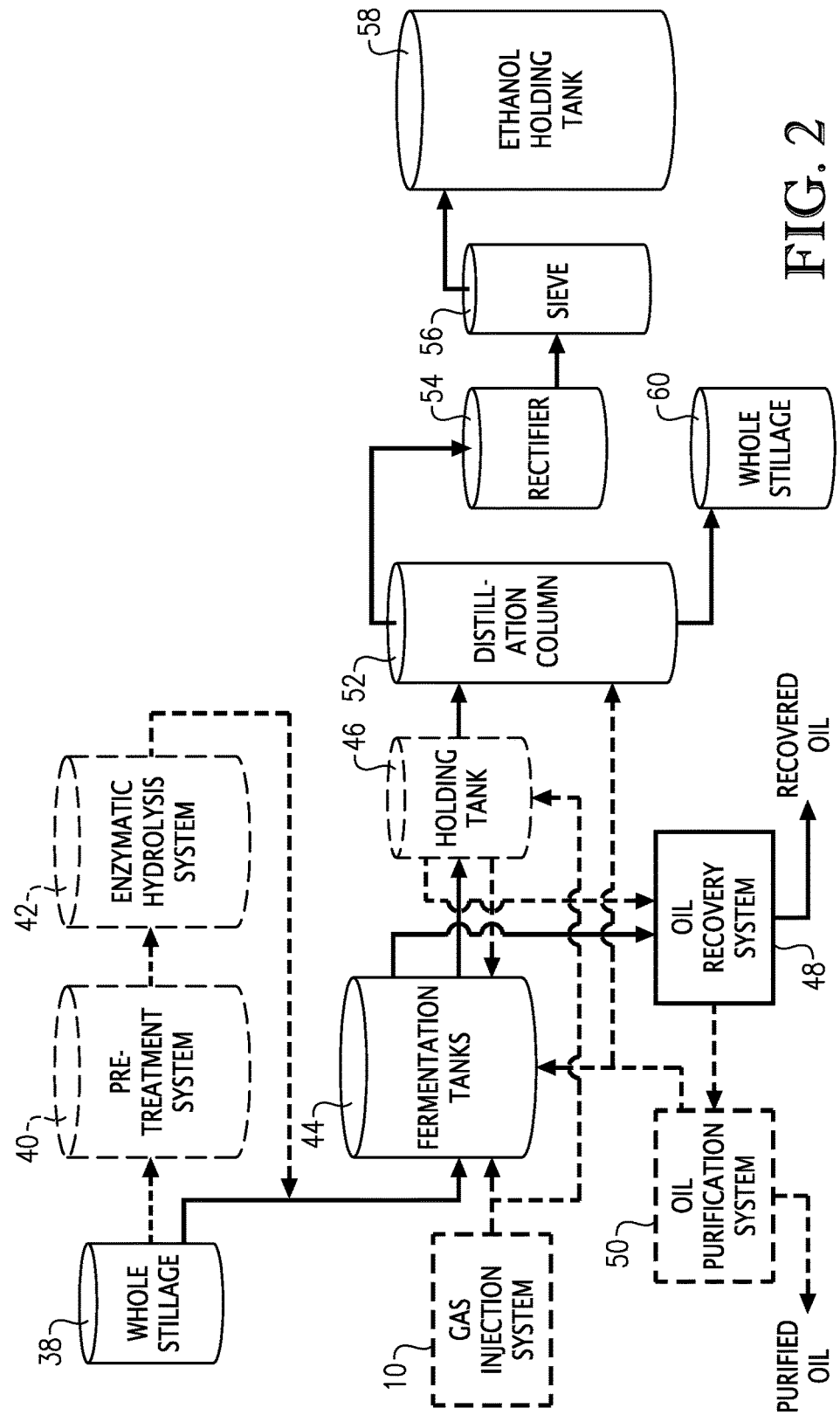
FIG. 2 is a flow diagram depicting an exemplary secondary fermentation process using whole stillage that utilizes an oil recovery step.

The secondary fermentation process is depicted in FIG. 2. It should be noted that the secondary fermentation process depicted in FIG. 2 can be modified, in whole or part, by other fermentation steps or components without departing from the scope of the present invention. As used herein, "secondary fermentation" refers to a fermentation process that utilizes a whole stillage as a feedstock. It should be noted that this whole stillage can include the whole stillage produced in the primary fermentation described above or, alternatively, it can include a whole stillage from a different fermentation process in which oil has not been previously removed therefrom.

Prior to the fermentation step, the whole stillage 38 can optionally be subjected to one or more pretreatments in a pretreatment system 40. The pretreatments can include, for example, steam explosion, acid hydrolysis, alkaline treatment, torrefaction, drying, grinding, soaking, or combinations thereof. The grinding can include, for example, wet milling or dry milling. These pretreatments can be utilized to break down some of the starch, cellulose and/or hemicellulose within the whole stillage into fermentable sugars. In certain embodiments, pretreating the cellulose and hemicellulose portions can make these components more prone to release the bound oils. Thus, this can allow for a greater yield of oil from the fiber components.

In various embodiments, the pretreatment can comprise adding an acid to the whole stillage to decrease its pH level; heating and pressurizing the whole stillage; holding the whole stillage under pressure and heat; removing pressure from the whole stillage to cause flashing; and cooling the whole stillage before the enzymes are added.

Additional pretreatment processes are further described in U.S. Patent Application Publication Nos. 2012/0045545, 2013/0149763, and 2013/0149750, the disclosures of which are incorporated herein by reference in their entireties.

The pretreatments can be used to break down at least a portion of the starch, cellulose, and/or hemicellulose in the whole stillage into fermentable sugars and can also release the bound oil within the fibers.

Turning again to FIG. 2, after being subjected to the optional pretreatment in the pretreatment system 40, the pretreated whole stillage can be optionally subjected to enzymatic hydrolysis in an enzymatic hydrolysis system 42. The enzymatic hydrolysis step can be used to break down at least a portion of the starch in the whole stillage into fermentable sugars and can further release some of the bound oil in the fibers of the whole stillage.

It should be noted that the enzymatic hydrolysis during the second fermentation can be more efficient compared to the hydrolysis step in the primary fermentation at breaking down the starch into fermentable sugars and releasing the bound oil from the fibrous matrix. This can be attributed to, at least partly, the lower starch concentrations found in the whole stillage compared to those in the initial biomass feedstock used in the primary fermentation and the greater exposure of the fibrous matrix in the whole stillage compared to the initial biomass feedstock in the primary fermentation.

Additionally or alternatively, the enzymatic hydrolysis can convert the cellulose portions of the fiber to fermentable sugars and also convert some of the hemicellulose to sugars. Hexose sugars, such as glucose, may be produced from the cellulose by the enzymatic hydrolysis. Pentose sugars, such as xylose, may be produced from the hemicellulose during the enzymatic hydrolysis.

During enzymatic hydrolysis, one or more enzymes can be added to the whole stillage to facilitate hydrolyzation of the starch and/or fibers in the whole stillage. In addition, various pH additives can be added such as, for example, ammonia, in order to create an ideal pH environment for the added enzymes. Different enzymes may be used to hydrolyze the starch, hemicellulose, and cellulose portions of the whole stillage. The enzymes can comprise, for example, a protease, xylanase, cellobiohydrolase, beta-glucosidase cellulase, amylase, hemicellulase, or combinations thereof. The enzymes may be added at a concentration in the range of about 0.001 to 0.5, 0.005 to 0.3, or 0.01 to 0.2 weight percent based on the dry weight of the solids.

As would be readily appreciated in the art, the specific or optimum conditions for enzymatic hydrolysis depend upon the particular enzymes used and are generally optimized to avoid denaturing the enzymes. For example, the enzymatic hydrolysis can occur at temperatures in the range of 100 to 250° F., 125 to 200° F., or 150 to 160° F. Additionally, the enzymatic hydrolysis can occur at pH in the range of about 2 to 8, 3 to 7, or 4 to 6. In various embodiments, the enzymatic hydrolysis for the second fermentation can occur at higher temperatures compared to the enzymatic hydrolysis step for the primary fermentation step.

The whole stillage, if subjected to a pretreatment, can be cooled prior to the hydrolysis treatment to a temperature that is more appropriate to facilitate the hydrolysis. The importance of the enzymatic hydrolysis step can depend on the severity of the pretreatment process. The less severe the pretreatment process, the more important the enzymatic hydrolysis can be.

Hemicellulose can be broken down with enzymes that are currently commercially available. Hemicellulases are generally used to hydrolyze hemicellulose and contain several different enzymes that hydrolyze specific bonds in hemicellulose. Hemicellulases are generally most effective at temperatures in the range of 155° F. to 185° F., with reduced activity at fermentation temperatures of 90° F. to 95° F. Since hemicellulose composition varies by feedstock, a hemicellulase that is most effective for the particular feedstock must be selected in embodiments where hydrolysis of the hemicellulose is desired.

If no fermentation of hemicellulose is being conducted, then the enzymatic hydrolysis step may not be required for fermentation. But the quality of the feed products, the ability to dry the feed, the viscosity of the stillage, and yield of oil can be greatly influenced by the hydrolysis of the hemicellulose. Due to its hydrophilic nature, the hemicellulose tends to bind liquids, especially water. The held water can increase viscosity, thereby increasing pumping requirements, and can increase the energy required to dry the final feed product. Oil can also become bound with the hemicellulose, which decreases oil yields. In addition, hemicellulose may be more digestible by monogastrics when hydrolyzed.

Cellulases are the enzymes that can be used to breakdown cellulose into its derivative sugars and can release the bound oil within the cellulose matrices. However, cellulose can be more difficult to convert to sugars during enzymatic hydrolysis because of its crystalline structure. The glucose is linked to form chains, with crosslinking between the chains. This crosslinking creates much of the difficulty in hydrolyzing cellulose; in effect, it can create a crystalline structure with a relatively small surface area to volume ratio.

Generally, the most effective way of hydrolyzing cellulose is to pretreat it prior to enzymatic hydrolysis as described above in order to rupture the fiber structure, which creates more surface area and decrystallizes the cellulose. Non-pretreated cellulose can have a structure with a very small surface area to volume ratio. This limits the number of areas available for enzymes to attach and liberate glucose from the structure. This determines the effective upper limit for cellulase dosing, thereby limiting the hydrolysis rate. By pretreating the cellulose, the crystalline structure can be disrupted and more areas for attack can be created. The hydrolysis rate is increased by decreasing polymerization of the cellulose and can be further increased by increased cellulase dosing.

The enzymatic hydrolysis of the pretreated cellulose can usually be accomplished in three steps. The first step involves cleaving the long chains of glucose from the cellulose using a whole cellulase, which randomly hydrolyzes links in the cellulose. Since this action is random, it can create anything from a single glucose unit to a chain that is a few thousand glucose units long. This is generally the cheapest portion of a cellulase formulation, but since it is random it does not produce free glucose units at a reliable rate. It does, however, create more chains for the next enzymes to act upon. The second step for hydrolyzing pretreated cellulose can be carried out by cellobiohydrolase. This enzyme can hydrolyze two units of glucose, termed cellobiose, from the end of a cellulose chain. Since this is not a random attack, the rate of production of cellobiose is predictable. The third step for hydrolyzing pretreated cellulose can be carried out by beta-glucosidase. This enzyme can act on the end of a cellulose chain and hydrolyze single units of glucose. The chain can be of any length from two units to thousands of units long. Generally, the best way to cost effectively hydrolyze cellulose is to balance the use of each one of these enzymes.

Depending on the nature of the enzyme used, the enzymatic hydrolysis can either be carried out during the subsequent fermentation step described below or as a separate step as described above in a separate tank where the temperature can be held higher so as to facilitate the activity level of the enzymes. The choice of a separate step or a simultaneous enzymatic and fermentation step depends on the activity of the enzymes used and on viscosity requirements. The whole stillage can become very viscous during the pretreatment steps, especially when cooled to fermentation temperature. It may be necessary, in some embodiments, to cool the whole stillage to an intermediate temperature where the viscosity is lower and then conduct enzymatic hydrolysis. The whole stillage can then be cooled to fermentation temperatures without excessive viscosity issues.

In various embodiments, the hydrolysis rates can determine the time necessary for the fermentation step. By increasing the rate of hydrolysis, the required fermentation time can be reduced. This can be attractive if a fermentation organism is capable of metabolizing the produced sugar as quickly as it is being liberated. The reduced fermentation time reduces the fermentation capacity required, thereby reducing capital costs.

Turning yet again to FIG. 2, after being subjected to the optional enzymatic hydrolysis in the system 42, the whole stillage can be subjected to a secondary fermentation in one or more fermentation tanks 44 to produce a secondary fermentation product. The yeast utilized in the secondary fermentation can include one or more types of yeasts and can depend on the sugar available for fermentation. For example, *Saccharomyces cerevisiae* is generally only able to ferment hexose sugars and, therefore, cannot generally use the pentose sugars unlocked from the hemicelluloses. Thus, in such embodiments, two outcomes can generally occur. Either an infectious organism begins to consume the pentose sugars and some of the hexose sugars, or no infection occurs and the pentose sugars remain in solution. In the first case, the final neutral detergent fiber content of the whole stillage produced by the secondary fermentation can be reduced and protein content can be increased, with a slight change in amino acid profile. In the second case, the neutral detergent fiber levels of the whole stillage produced by the secondary fermentation can remain higher, but can exhibit a reduction in the percentage of protein.

Due to the diversity of sugars that can be found in the whole stillage, different combinations of yeasts may need to be utilized in the secondary fermentation to maximize sugar conversion. In one or more embodiments, the yeasts are selected from the group consisting of *Saccharomyces cerevisiae, Pichia stipitis, Candida shehatae*, and combinations thereof. In certain embodiments, the yeast utilized in the secondary fermentation can be the same or different from the yeast utilized in the primary fermentation step. In one embodiment, the yeast is *Saccharomyces cerevisiae*.

In various embodiments, the secondary fermentation can occur in the same system and/or vessel as the primary fermentation. Alternatively, the secondary fermentation can occur in a separate system and/or vessel than the primary fermentation.

The conditions of the secondary fermentation can vary depending on the sugars present in the feedstock and the effects of the previous pretreatment and hydrolysis steps (if utilized). For example, the secondary fermentation can occur over a time period in the range of 12 to 150, 24 to 130, or 36 to 110 hours. Generally, at least 20 hours of fermentation time is necessary to ferment about 80 percent of the sugars in the whole stillage; however, longer time periods can be necessary in order to ferment the sugars that can be found in hemicellulose and cellulose. Fermentation usually ceases when the feedstock for the yeasts becomes exhausted. If fermentation is extended beyond this point, then the yeast can go through autolysis and begin to consume their own structural carbohydrates. This can increase the protein levels of the whole stillage byproduct but can have very little influence on final ethanol yields.

Furthermore, depending on the type of yeasts used, secondary fermentation can occur at a temperature in the range of 50 to 140, 70 to 120, or 80 to 97° F. In addition, the secondary fermentation can occur at a pH in the range of about 3 to 8, 3.5 to 6, or 4 to 5.

During the first 4 to 6 hours of the fermentation, little to no ethanol can be produced since it is generally during this phase that the yeast are reproducing. In certain embodiments, the starch is the most accessible sugar during these early stages and, therefore, the production of the yeast cells can be generally fueled by the starch. During the post-reproduction phase of fermentation, the yeast can begin to produce ethanol. This can occur as glucose is slowly liberated from the cellulose chains.

Like the primary fermentation product, the secondary fermentation product can comprise multiple types of alcohols and other various solid and liquid byproducts. However, ethanol is usually the most important product produced during the secondary fermentation process. In one or more embodiments, the secondary fermentation product can comprise at least about 1, 2, 3, or 3.5 and/or not more than about 25, 20, 15, or 10 weight percent of ethanol. More particularly, the secondary fermentation product can comprise in the range of about 1 to 25, 2 to 20, 3 to 15, or 3.5 to 10 weight percent of ethanol.

Furthermore, due to the lower starch concentrations of the whole stillage, the ethanol concentration produced during the secondary fermentation can also be low, thereby allowing the yeast to have longer access to the sugars in the whole stillage. Consequently, in various embodiments, this can lead to higher yields of ethanol per bushel of grain. For example, the secondary fermentation can produce at least about 0.15, 0.3, 0.35, or 0.4 and/or not more than about 1.5, 1.0, 0.8, or 0.6 gallons of ethanol per bushel of grain. More particularly, the secondary fermentation can produce in the range of about 0.15 to 1.5, 0.3 to 1.0, 0.35 to 0.8, or 0.4 to 0.6 gallons of ethanol per bushel of grain. Furthermore, the secondary fermentation can convert at least 75, 80, 85, or 90 percent of the starch in the whole stillage into the secondary fermentation product.

In various embodiments, the secondary fermentation can convert at least a portion of the cellulose and/or hemicellulose in the whole stillage into fermentation products. For example, the secondary fermentation can convert at least about 30, 40, 50, 60, or 70 percent of the cellulose originally found in the whole stillage into the secondary fermentation product. Additionally or alternatively, the secondary fermentation can convert at least about 30, 40, 50, 60, or 70 percent of the hemicellulose originally found in the whole stillage into the secondary fermentation product.

Other byproducts included in the secondary fermentation product can include, for example, glycerol, acetic acid, lactic acid, and carbon dioxide. In one or more embodiments, the secondary fermentation product can comprise at least about 0.001, 0.005, or 0.01 and/or not more than about 1.5, 0.5, or 0.1 weight percent of glycerol. More particularly, the secondary fermentation product can comprise in the range of about 0.001 to 1.5, 0.005 to 0.5, or 0.01 to 0.1 weight percent of glycerol. Furthermore, the secondary fermentation product can comprise at least about 0.0001, 0.001, or 0.01 and/or not more than about 0.5, 0.3, or 0.2 weight percent of acetic acid. More particularly, the secondary fermentation product can comprise in the range of about 0.0001 to 0.5, 0.001 to 0.3, or 0.01 to 0.2 weight percent of acetic acid. In addition, the secondary fermentation product can comprise at least about 0.001, 0.005, or 0.01 and/or not more than about 2, 1.5, or 1 weight percent of lactic acid. More particularly, the secondary fermentation product can comprise in the range of about 0.001 to 2, 0.005 to 1.5, or 0.01 to 1 weight percent of lactic acid. It should be noted that the above weight percentages are based on the total weight of the fermentation product unless otherwise noted.

Furthermore, the secondary fermentation product can comprise one or more oils derived from the hemicellulose, cellulose, and residual oil-containing biomass feedstock in the whole stillage. In one or more embodiments, the secondary fermentation product can comprise at least about 0.1, 0.5, 1, or 2 and/or not more than 30, 25, 20, or 10 weight percent of oil. More particularly, the secondary fermentation product can comprise in the range of about 0.1 to 30, 0.5 to 25, 1 to 20, or 2 to 10 weight percent of oil.

Moreover, in various embodiments, at least a portion of the oil in the secondary fermentation product can be free oil. In one or more embodiments, the secondary fermentation product can comprise at least about 0.1, 0.5, 1, or 2 and/or not more than 30, 25, 20, or 10 weight percent of free oil. More particularly, the secondary fermentation product can comprise in the range of about 0.1 to 30, 0.5 to 25, 1 to 20, or 2 to 10 weight percent of free oil.

As previously noted, the oil in the secondary fermentation product has commercial value and, thus, it is generally desirable to remove this byproduct at some point from the fermentation products. Unlike the prior art processes, the processes and systems described herein are able to separate and extract the oil in the secondary fermentation product prior to removing the ethanol from the fermentation product.

As described above, the free oil in the secondary fermentation product can be brought to the surface of the fermentation product by introducing a gas into the fermentation product. In such embodiments, the introduced gas can cause the oil in the fermentation product to rise to the top of the fermentation product, thereby making it easier to recover. Thus, in various embodiments, a gas may be introduced into the secondary fermentation product in order to separate the fermentation product into an oil-poor component and an oil-rich component comprising the free oil.

In one or more embodiments, the gas introduced into the secondary fermentation product can be at least partially derived from, or alternatively, entirely derived from, the gas produced during the secondary fermentation by the yeasts and/or a gas from the gas injection system 10. The gas can comprise one or many types of gases. In various embodiments, the gas comprises carbon dioxide, air, nitrogen, or combinations thereof. In certain embodiments, the gas comprises carbon dioxide.

In various embodiments, the gas can be introduced into the secondary fermentation product through the use of a gas injection system 10, which can pump a gas stream into the bottom of the fermentation tank 44 thereby allowing the introduced gas to pass through the secondary fermentation product. The gas injection system 10 can be configured to pump the gas into the fermentation tank 44 at a sufficient pressure that can overcome the head pressure of the fermentation tank. In certain embodiments, the gas injection system can be the same system that was used in the primary fermentation. Alternatively, the gas injection system can be different from the gas injection system utilized during the primary fermentation.

In various embodiments, the gas introduced into the secondary fermentation product can be at least partially derived, or alternatively, entirely derived from the gases produced during fermentation by the yeasts. As the yeasts ferment the sugars in the feedstock, various gases can be produced, such as carbon dioxide. For instance, the secondary fermentation can produce in the range of about 0.1 to 3, 0.3 to 2.5, 0.5 to 1.5, or 0.7 to 1.2 pounds of carbon dioxide per bushel of grain.

In certain embodiments, it may be difficult or impose a safety risk to remove oil from the top of an active fermenter. In these cases, it may be reasonable to process the fermentation product through any number of additional steps until it is safe to remove the oil from the top of tank. These additional process steps are discussed below and can include, for example, distillation, pressing, and centrifugation. The tankable liquids left after these processes can then be subjected to gas bubbling by means of the gas injection system 10 in an optional holding tank 46 as shown in FIG. 2.

The optional holding tank 46 as shown in FIG. 2 can be used to hold the fermentation product after it has been subjected to any number of post-fermentation treatment steps, but prior to being separated into oil-poor and oil-rich components as described above. In various embodiments, the secondary fermentation product can be introduced into a holding tank 46 where a gas can be introduced into the fermentation product, thereby separating the fermentation product into the oil-poor and oil-rich components discussed above. In such embodiments, the gas can be introduced into the holding tank 46 from the gas injection system 10. It should be noted that the gas introduced into the holding tank will generally come from the gas injection system since most of the fermentation will be finished by this point. An advantage of the gas injection system is that the secondary fermentation product can be separated in non-fermentation tanks.

During the gas introduction steps, the gas can be introduced into the fermentation product while in the fermentation tanks 44 and/or holding tank 46 at a sufficient rate so as to cause the fermentation product to separate into the oil-poor and oil-rich components. In various embodiments, the gas can be introduced into the fermentation product at a rate of at least about 1, 5, 10, 15, 20, 25, 30, 35, 40, or 45 $cm^3$/min and/or not more than about 1,000, 750, 500, 400, 350, 300, 250, 200, 150, or 100 $cm^3$/min. More particularly, the gas can be introduced into the fermentation product at a rate in the range of about 1 to 1,000, 5 to 750, 10 to 500, 15 to 400, 20 to 350, 25 to 300, 30 to 250, 35 to 200, 40 to 150, or 45 to 100 $cm^3$/min. Furthermore, the gas can be introduced into the fermentation product over a time period of at least 0.1, 0.5, 1, 2, or 3 hours and/or not more than 24, 12, 10, 8 or 6 hours. More particularly, the gas can be introduced into the fermentation product over a time period in the range of 0.1 to 24 hours, 0.5 to 12 hours, 1 to 10 hours, 2 to 8 hours, or 3 to 6 hours.

Furthermore, it has been observed that agitation rates within the fermentation tanks 44 and/or holding tank 46 can have an effect on the separation of the secondary fermentation product into the oil-poor and oil-rich components during the gas introduction steps. It was observed that holding agitation rates to a low level would allow at least a portion of the free oil to float to the top of the fermentation product. In such cases, as long as the agitation rates are not high enough to cause a downward velocity that overcomes the buoyancy of the oil, the free oil can continue to float and be recovered. If the fermentation product is subjected to excessive agitation, then the free oil can be redistributed within the fermentation product as bound oil.

In many embodiments, the fermentation tanks 44 can have an agitator as described above. In various embodiments, the agitation rate of the agitator during the gas introduction step can be less than 100, 50, 20, 5, or 1 RPM. Furthermore, in embodiments where the gas introduction step occurs in the fermentation tank, the agitation speed of the agitator during the gas introduction can be at least 50, 75, 90, or 99 percent less than the agitation speed of the agitator during fermentation prior to the gas being introduced.

In various embodiments, the fermentation product is subjected to substantially no agitation or no agitation during the gas introduction step.

It should be noted that the gas introduction step can occur during fermentation or after fermentation when the yeasts have finished converting the sugars into the various fermentation products. As noted above, the gas introduction step, and the subsequent removal of the oil-rich component, can occur in the fermentation tanks 44 or holding tank 46.

Turning back to FIG. 2, after separating the primary fermentation into the oil-poor and oil-rich components in the fermentation tanks 44 and/or holding tank 46, the oil-rich component can be recovered from the fermentation tanks 44 and/or the holding tank 46 using an oil recovery system 48. The oil recovery system 48 can comprise any system or means known in the art that are capable of removing the top oil-rich component from the tanks such as, for example, a pumping apparatus or industrial pipette. For example, the oil recovery system could comprise a pipe and pump connected to the tank that could remove the top layer comprising the oil-rich component. In such embodiments, the pipe and pump could also remove the top 1% of the fermentation product to ensure that most, if not all, of the free oil is recovered from the fermentation tank.

The recovered oil-rich component removed by the oil recovery system 48 can contain the majority of the free oil originally found in the fermentation product. For example, the recovered oil-rich component can comprise at least about 25, 50, 75, 90, 95, or 99 percent of the free oil originally present in the fermentation product. Furthermore, the recovered oil-rich component can comprise at least about 25, 50, 75, 85, 90, 95, or 99 weight percent of oil that was derived from the oil-containing biomass feedstock used in the primary fermentation process. Moreover, the recovered oil-rich component may comprise an oil content by weight percentage that is at least 25, 50, 75, or 90 percent greater than the oil content by weight percentage of the secondary fermentation product.

In addition to its high oil content, the recovered oil-rich component may also comprise some incidental fermentation byproducts. These incidental fermentation byproducts can include any of the other products produced during fermentation such as, for example, ethanol, glycerol, acetic acid, lactic acid, and unconverted biomass feedstock. Generally, the recovered oil-rich component can comprise less than about 20, 10, 5, 1, or 0.1 weight percent of incidental fermentation byproducts. Moreover, the recovered oil-rich component can comprise less than about 20, 10, 5, 1, or 0.1 weight percent of water.

In various embodiments, it may be desirable to further treat the recovered oil-rich component in an oil purification system 50 as shown in FIG. 2 in order to concentrate the oil and remove the undesirable byproducts therein. The oil purification system 50 can comprise any system known in the art that is capable of purifying oil such as, for example, a filter membrane, a centrifuge, a settling tank, or a combination thereof. In one or more embodiments, the oil purification system can be the same system used during the primary fermentation. Alternatively, the secondary fermentation can utilize a different oil purification system than the primary fermentation.

The purified oil from the oil purification system 50 can comprise at least about 50, 85, 95, 99, or 99.9 weight percent of oil. Furthermore, the purified oil can comprise less than about 5, 3, 1, 0.1, or 0.01 weight percent of water. Moreover, the purified oil can comprise less than about 10, 5, 3, 1, or 0.1 weight percent of incidental fermentation byproducts.

In various embodiments, the secondary fermentation can produce at least about 0.25, 1, 1.25, or 1.5 and/or not more than about 4, 3, 2.5, or 2 pounds of recovered oil per bushel of grain. More particularly, the secondary fermentation can produce in the range of about 0.25 to 4, 1 to 3, 1.25 to 2.5, or 1.5 to 2 pounds of recovered oil per bushel of grain. Similarly, the secondary fermentation can produce at least about 0.1, 0.2, 0.3, or 0.7 and/or not more than about 5, 4, 3, or 1.2 liters of recovered oil per bushel of grain. More particularly, the secondary fermentation can produce in the range of about 0.1 to 5, 0.2 to 4, 0.3 to 3, or 0.4 to 1 liters of recovered oil per bushel of grain.

As noted above, the incidental fermentation product removed by the oil purification system 50 can be recycled back to the fermentation tank 44 for further conversion and/or sent to the distillation column 52 for further processing.

As shown in FIG. 2, after recovering the oil-rich component, the oil-poor component remains in the fermentation tank 44 and/or holding tank 46. The remaining oil-poor component generally comprises the non-oil byproducts produced during fermentation. For example, the oil-poor component generally comprises ethanol, glycerol, acetic acid, lactic acid, unconverted biomass feedstock, and other fermentation-derived alcohols. In one or more embodiments, the oil-poor component can comprise at least about 10, 15, 20, or 25 and/or not more than about 70, 60, 50, or 40 weight percent of ethanol. More particularly, the oil-poor component can comprise in the range of about 10 to 70, 15 to 60, 20 to 50, or 25 to 40 weight percent of ethanol. Furthermore, the oil-poor component comprises less than 20, 10, 5, or 1 weight percent of oil. Additionally or alternatively, the oil-poor component can comprise an oil content by weight percentage that is at least 25, 50, 75, or 90 percent lower than the oil content by weight percentage of the secondary fermentation product. In embodiments where a holding tank 46 is utilized, the remaining oil-poor component in the holding tank 46 can be sent to the fermentation tanks 44 for further fermentation if necessary.

Turning again to FIG. 2, the remaining oil-poor component in the fermentation tanks 44 or holding tank 46 can be transferred to one or more distillation columns 52. In the distillation columns 52, the ethanol can be removed from the oil-poor component and transferred to one or more rectifiers 54 and molecular sieves 56 to remove moisture therefrom. The final alcohol can then be transferred to one or more ethanol holding tanks 58 where it may be denatured before use as a fuel or fuel additive.

The liquid and solid mixture that remains in the distillation columns 52 after the alcohol has been removed is the secondary whole stillage. The secondary whole stillage generally settles to the bottom of the distillation columns 52 and can then be transferred to one or more whole stillage holding tanks 60.

Although not shown in FIG. 2, the secondary whole stillage produced by the secondary fermentation step can be further treated in post-fermentation processes. These processes are discussed above in regard to the whole stillage of the primary fermentation.

The primary fermentation and secondary fermentation steps described herein can be used to convert the majority of the starch, cellulose, and/or hemicellulose originally found in the biomass feedstock into useful products. For example, the combined output of the primary fermentation and the secondary fermentation can produce at least about 2.65, 2.8, 2.95, or 3.1 and/or not more than about 4.0, 3.7, 3.5, or 3.3 gallons of ethanol per bushel of grain. More particularly, the combined output of the primary fermentation and the secondary fermentation can produce in the range of about 2.65 to 4.0, 2.8 to 3.7, 2.95 to 3.5, or 3.1 to 3.3 gallons of ethanol per bushel of grain.

Furthermore, the process described herein can also improve grain oil recovery by breaking down and fermenting the fiber in the fat-rich germ portion of the grains. In prior art processes, the oil tends to become trapped within the fiber matrix of the germ, thus making it difficult to remove. Most fermentation plants report yields of 15 to 35% of the total oil capable of being recovered. By breaking down the fiber as described herein, substantially all of the grain oil can be recovered. For example, the combined output of the primary fermentation and the secondary fermentation can produce at least about 0.25, 1, 1.25, or 1.5 and/or not more than about 5, 4, 2.5, or 2 pounds of oil per bushel of grain. More particularly, the combined output of the primary fermentation and secondary fermentation can produce in the range of about 0.25 to 5, 1 to 4, 1.25 to 2.5, or 1.5 to 2.0 pounds of oil per bushel of grain.

Based on the above, the oil recovery processes and systems described herein contain multiple advantages. Compared to the prior art, less equipment and energy can be required to separate and recover the oil from the fermentation product. For example, the processes described herein can remove the need for a centrifugation step and other heating or chemical treatments commonly used in prior art processes. Thus, the inventive processes and systems can therefore save on both equipment and energy costs.

Furthermore, by drawing the oil off during the fermentation stage as described above, there is less chance of oil loss through other parts of the process. In the prior art processes, the distillation, decanting, and evaporation steps, along with the associated heating and pumping, can disperse the oil into microscopic droplets. Consequently, these droplets can be very difficult to separate, thereby making a significant portion of the oil more difficult to recover. Thus, this can greatly reduce oil yields.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

As used herein, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. Thus, the present invention can include a variety of combinations and/or integrations of the embodiments described herein.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. A method for recovering an oil from a fermentation product, the method comprising: (a) fermenting an oil-containing biomass feedstock to thereby produce a fermentation product comprising an oil; (b) introducing a gas into the fermentation product to thereby form an oil-poor component and an oil-rich component; and (c) separating the oil-rich component from the oil-poor component to thereby produce a recovered oil-rich product, wherein the gas is introduced into the fermentation product at a rate of 5 to 1,000 cm$^3$/min and the fermenting of step (a) and the introducing of a gas of step (b) occur in a container comprising an agitator, wherein the agitator operates at a predetermined agitation rate during the fermenting of step (a) and a predetermined agitation rate during the introducing of the gas of step (b), wherein the predetermined agitation rate during the introducing step of the gas of (b) is at least 50 percent less than the predetermined agitation rate during the fermenting of step (a).

2. The method of claim 1, wherein the gas is introduced over a period of 0.1 to 24 hours.

3. The method of claim 1, wherein the recovered oil-rich product comprises at least about 75 weight percent of oil.

4. The method of claim 1, wherein the recovered oil-rich product comprises at least about 50 percent of the oil originally present in the fomentation product.

5. The method of claim 1, wherein at least a portion of the gas is produced by a gas sparger, gas diffuser, aeration turbine, venturi tube, or a combination thereof.

6. The method of claim 1, wherein the gas comprises carbon dioxide.

7. The method of claim 1, wherein the oil-containing feedstock comprises a grain.

8. The method of claim 1, further comprising purifying the recovered oil-rich product to produce a purified oil.

\* \* \* \* \*

UNITED STATES PATENT AND TRADEMARK OFFICE
CERTIFICATE OF CORRECTION

| | | |
|---|---|---|
| PATENT NO. | : 9,752,165 B2 | Page 1 of 1 |
| APPLICATION NO. | : 14/176988 | |
| DATED | : September 5, 2017 | |
| INVENTOR(S) | : Travis Brotherson | |

It is certified that error appears in the above-identified patent and that said Letters Patent is hereby corrected as shown below:

In the Claims

Column 22, Claim 4, Line 32:
Please correct "fomentation" to read -- fermentation --

Signed and Sealed this
Twenty-sixth Day of June, 2018

Andrei Iancu
*Director of the United States Patent and Trademark Office*